United States Patent [19]

Patsalos et al.

[11] Patent Number: 5,607,390
[45] Date of Patent: Mar. 4, 1997

[54] DIALYSIS PROBE

[75] Inventors: Philip N. Patsalos, London; Mark L. O'Connell, St. Neots, both of England

[73] Assignee: Institute of Neurology, London, Great Britain

[21] Appl. No.: 446,866

[22] PCT Filed: Dec. 10, 1993

[86] PCT No.: PCT/GB93/02526

§ 371 Date: Jun. 20, 1995

§ 102(e) Date: Jun. 20, 1995

[87] PCT Pub. No.: WO94/13195

PCT Pub. Date: Jun. 23, 1994

[30] Foreign Application Priority Data

Dec. 15, 1992 [GB] United Kingdom .......... 9226147

[51] Int. Cl.$^6$ ........................................ A61M 1/00
[52] U.S. Cl. .................. 604/29; 604/27; 604/174; 604/264
[58] Field of Search ............... 604/27, 28, 29, 604/43, 280–284, 246, 264, 174; 128/769, 768, 760, 632

[56] References Cited

U.S. PATENT DOCUMENTS

| | | | |
|---|---|---|---|
| 3,572,315 | 3/1971 | Cullen, II | 128/2 |
| 3,824,157 | 7/1974 | Macur | 204/1 T |
| 4,694,832 | 9/1987 | Ungerstedt | 128/632 |
| 4,863,432 | 9/1989 | Kvalo | 604/177 |
| 4,962,757 | 10/1990 | Stefan | 128/DIG. 28 |
| 5,106,365 | 4/1992 | Hernandez | 604/27 |
| 5,115,817 | 5/1992 | Sarstedt | 128/764 |
| 5,441,481 | 8/1995 | Mishra et al. | 604/29 |
| 5,472,432 | 12/1995 | Martin | 604/29 X |
| B1 4,772,269 | 5/1992 | Twardowski et al. | 604/175 |

FOREIGN PATENT DOCUMENTS

| | | |
|---|---|---|
| 1595079 | 8/1981 | United Kingdom . |
| 2130916 | 6/1984 | United Kingdom . |
| WO90/14791 | 12/1990 | WIPO . |
| WO92/18191 | 10/1992 | WIPO . |

*Primary Examiner*—John D. Yasko
*Attorney, Agent, or Firm*—Burns, Doane, Swecker & Mathis LLP

[57] ABSTRACT

A dialysis probe for insertion into the human or animal body includes a tubular dialysis membrane (2) closed at its distal end (3); an inlet tube (4) for supplying perfusion fluid into the body of the dialysis membrane (2); and an outlet tube (5) for the exit of perfusion fluid from the body of the dialysis membrane, the inlet and outlet tubes being provided at the proximal end of the tubular dialysis membrane (2) and making sealed connection with the interior of the dialysis membrane. An anchoring member (7, 20) is provided at the proximal end of the probe and in a first embodiment comprises a plate-like member for securing directly to the body of the subject, and in a second embodiment comprises a stopper cap (21, 22, 23, 24) for plugging a cannula itself attached to the body of the subject. The anchoring member has all the remaining component parts of the probe bounded, directly or indirectly, to it.

19 Claims, 3 Drawing Sheets

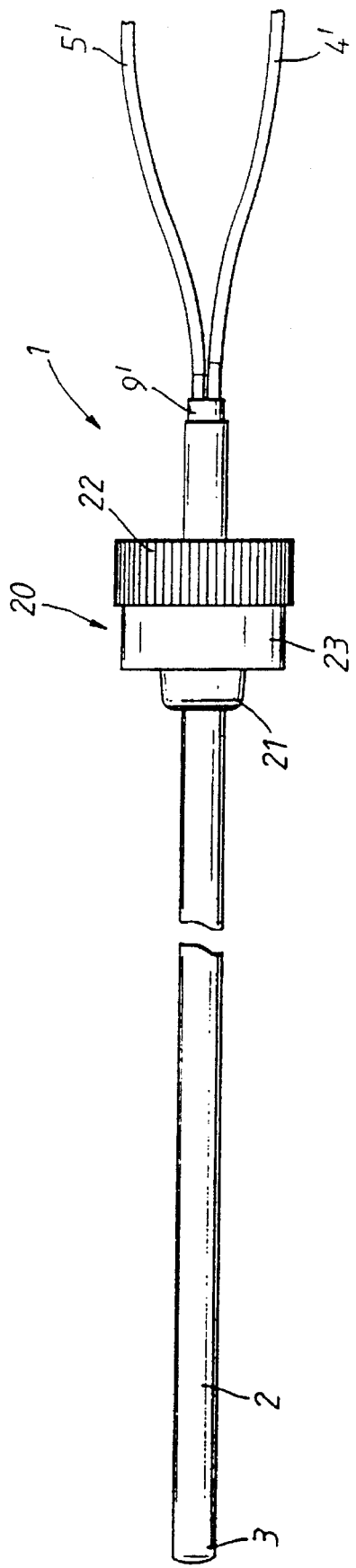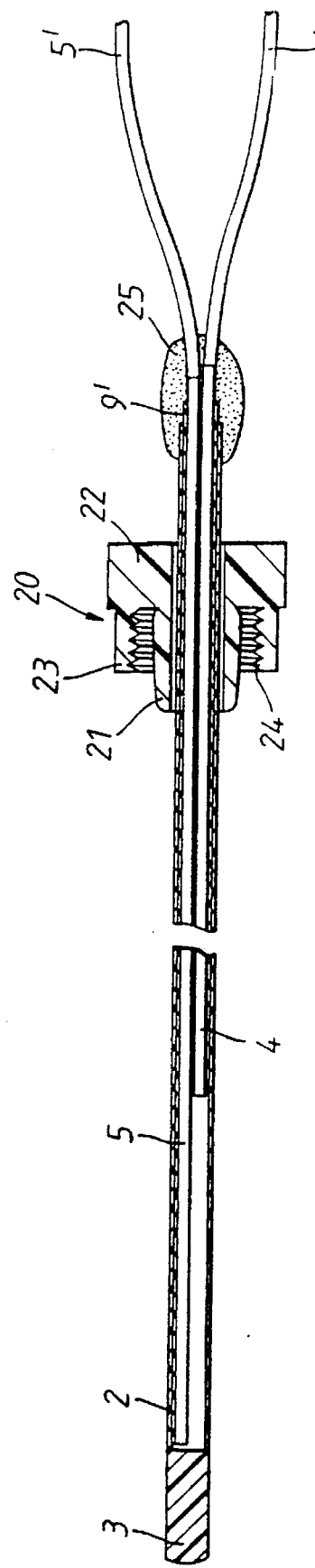

DIALYSIS PROBE

This invention relates to dialysis probes.

One known form of dialysis probe is described in U.S. Pat. No. 5,106,365 and an explanation is given there of the uses and problems associated with microdialysis probes.

It is an object of the invention to provide a dialysis probe that has increased safety in use.

The present invention provides a dialysis probe for insertion into the human or animal body, the probe comprising:

a tubular dialysis membrane closed at one end, hereafter referred to as the distal end;

an inlet tube for supplying perfusion fluid into the body of the dialysis membrane; and an outlet tube for the exit of perfusion fluid from the body of the dialysis membrane, the inlet and outlet tubes being provided at the other end, hereafter referred to as the proximal end, of the tubular dialysis membrane and making sealed connection with the interior of the dialysis membrane, characterized in that:

an anchoring member is provided at the proximal end of the probe;

each of the dialysis membrane, the inlet tube and the outlet tube is bonded to the anchoring member; and the anchoring member includes attachment means for securing it to the outside of the body of the subject.

Such a probe has increased safety in use because the provision of the anchoring member at the proximal end of the probe, the bonding of the components to it, and the securing to the outside of the body of the subject together greatly reduce the risk that any part of the probe will break free and be lost in the body of the subject. The loss of a part of the probe into, for example, a vein or artery could readily lead to fatal consequences for the subject and thus a probe according to the invention can be used within a vein or artery with relative safety.

Advantageously, the attachment means is arranged to be secured indirectly to the body of the subject and comprises a stopper surrounding the dialysis membrane for plugging the lumen of a cannula secured to the outside of the body of the subject. Such an arrangement enables the probe to be used with a cannula left in situ for an extended period and usable for other purposes, such as the introduction of therapeutic or diagnostic agents, as well as for the introduction of a probe according to the invention. Thus, the trauma of the repeated introduction of a cannula can be avoided.

Preferably, the stopper is a cap comprising a central plug portion to enter the interior of the cannula, an annular head portion extending transversely to the axis of the probe, and an annular wall projecting from the annular head portion towards the distal end of the probe to engage the exterior of the cannula. That provides a very simple means of securing the probe to a cannula.

The interior of the annular wall may be provided with a screw thread. Such an arrangement provides additional security when used with a cannula arranged to receive a screw-threaded cap.

Preferably, the stopper is made of resilient plastics material. By that means a secure seal in the lumen of the cannula can readily be obtained.

The dialysis membrane may project beyond the attachment means at the proximal end of the probe.

In a different form of construction, the attachment means is arranged to be secured directly to the body of the subject and each of the dialysis membrane, the inlet tube and the outlet tube is bonded directly to the anchoring member.

Advantageously, one end of a respective flexible connecting tube is connected to the proximal end of each of the inlet and outlet tubes, and the said one end of each connecting tube is bonded to the anchoring member. By that means connection to external apparatus is facilitated and the integrity of the connection between the connecting tubes and the inlet and outlet tubes ensured.

Advantageously, an impermeable sheath is provided on the interior or the exterior of the tubular dialysis membrane and extends from the proximal end of the probe to a position part way along the length of the dialysis membrane. Such a sheath prevents dialysis from taking place near the proximal end of the probe where contact with the surface tissues of the subject may falsify the results obtained from using the probe.

The sheath may, for example, extend to within 5 centimeters, within 2 centimeters or within 1 centimeter of the distal end of the dialysis membrane.

The sheath may comprise an impermeable coating on the outside of the dialysis membrane or it may comprise a sleeve mounted on the dialysis membrane and bonded to the anchoring member. The use of a coating or a sleeve bonded to the anchoring member are each relatively safe ways of providing a sheath that is not in danger of breaking off into the body of the subject.

Advantageously, the dialysis membrane and the sheath are both flexible. Such an arrangement is suited to a long probe, for example, one which is passed via a vein in the arm of a patient into a chamber of the heart Advantageously, the outlet tube extends within the dialysis membrane from the proximal end of the probe to a point close to the distal end of the dialysis membrane. Such an arrangement avoids deadspace in the body of the membrane when measurements from the tip are required.

The outlet tube may extend to within 5 centimeters, within 2 centimeters or within 1 centimeter of the distal end of the dialysis membrane.

Preferably, the sheath extends to a point close to but before the distal end of the outlet tube. With such an arrangement, the outlet tube and sheath co-operate in defining the sampling zone.

Preferably, the inlet tube enters the proximal end of the dialysis membrane. If, however, the diameter of the dialysis membrane is so small that it is impractical for both the inlet and outlet tubes to enter it, the inlet tube may remain outside the dialysis membrane and have its end connected to the mouth of the membrane.

Preferably, the inlet tube extends within the dialysis membrane by more than half the length of the dialysis membrane. Such an arrangement makes good use of the distal end of the membrane for sampling.

Advantageously, the anchoring member comprises a plate-like member. Such a plate-like member can be readily secured to the subject using adhesive tape.

Advantageously, the axis of the dialysis membrane is substantially parallel to the plane of the plate-like member. Such an arrangement is suited for a probe for insertion into a vein of the fore-arm, for example.

The inlet and outlet tubes are preferably arranged side-be-side with their axes substantially parallel to the plane of the plate-like member. Such an arrangement permits compact and secure bonding of the tubes to the anchoring member.

Advantageously, the anchoring member comprises a resilient flexible plate-like member defining first and second wings extending on opposite sides of the longitudinal axis of the tubular dialysis membrane, the flexibility of the plate-like member permitting the wings to be bent together for gripping between the finger and thumb for deployment of the probe. Such an arrangement is particularly convenient to deploy and particularly convenient to tape to the subject.

Advantageously, each wing includes a respective aperture to permit suturing the probe to the subject. By that means a very high degree of security against displacement of the probe can be achieved.

Preferably, the plate-like member is made of plastics material.

The plate-like member may be moulded about the dialysis membrane, the inlet and outlet tubes and, where provided, the sheath. Such an arrangement is simple to manufacture using plastics material for the anchoring member.

The plate-like member may be formed of two parts, one part overlying the other, and the dialysis membrane, the inlet and outlet tubes and, where provided, the sheath may be located between the two parts. Such an arrangement can be readily assembled using a suitable adhesive.

Preferably, one part of the plate-like member is substantially flat and the other part is substantially flat except for a central section accommodating the dialysis membrane, the inlet and outlet tubes and, where provided, the sheath. Such an arrangement is neat and compact.

The diameter of the dialysis membrane may be in the range 1 to 10 millimeters or 1 to 5 millimeters inclusive. Such a probe is suitable for insertion into a major vein or artery.

The diameter of the dialysis membrane may be in the range 0.2 to 1.0 millimeters inclusive. Such a probe is well suited for insertion into a vein or artery of small or moderate size.

The diameter of the dialysis membrane may be in the range 0.2 to 0.5 millimeters inclusive. Such a probe is suitable for insertion into a part of the body where there is a serious risk of permanent damage arising from the insertion of a probe. Desirably, the probe may be made even finer by giving the dialysis membrane a diameter in the range 0.1 to 0.2 millimeters or 0.05 to 0.1 millimeters inclusive.

Preferably, the distal end of the dialysis membrane is closed by the material of the membrane itself. Such an arrangement is safer than providing a separate plug, which might become detached, at the tip of the membrane.

A dialysis probe constructed in accordance with the invention will now be described, by way of example only, with reference to the accompanying drawings, in which:

FIG. 9 is a diagrammatic side view of a second probe embodying the invention; and FIG. 10 is a cross-section through the probe of FIG. 9.

Figure 1:
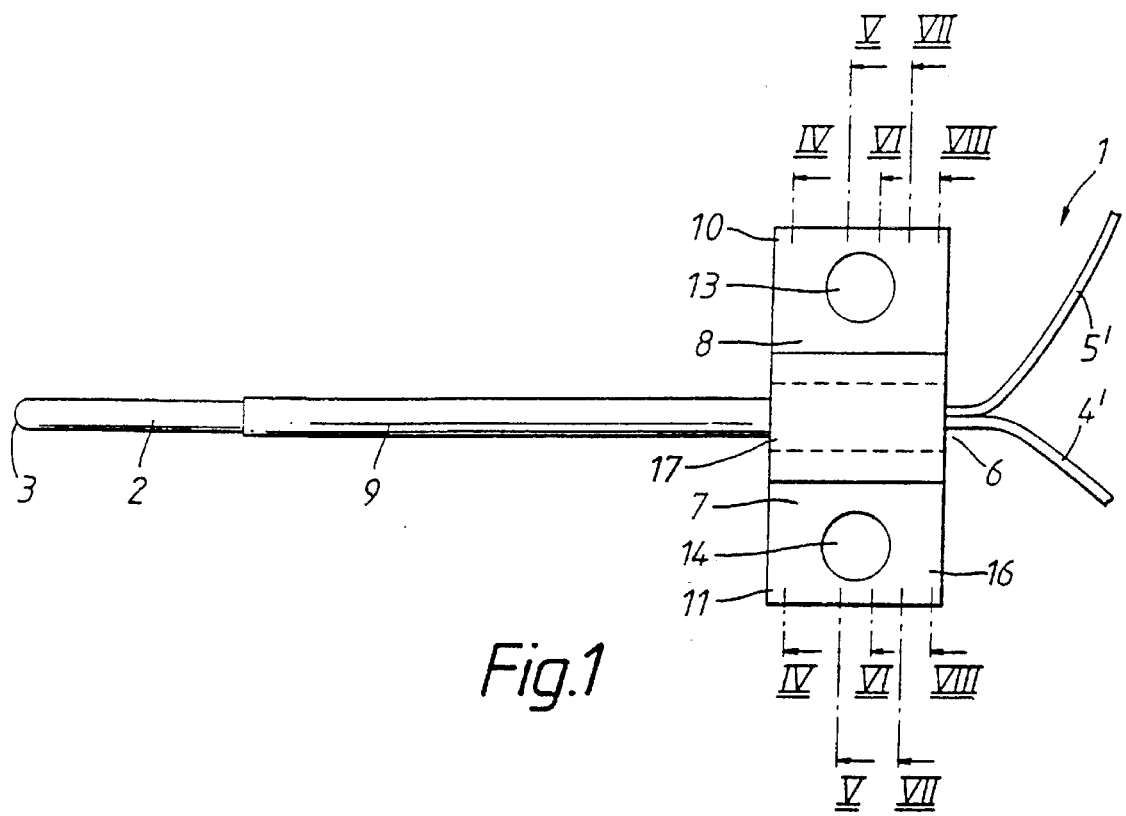
FIG. 1 shows a plan view of the probe.
Figure 2:
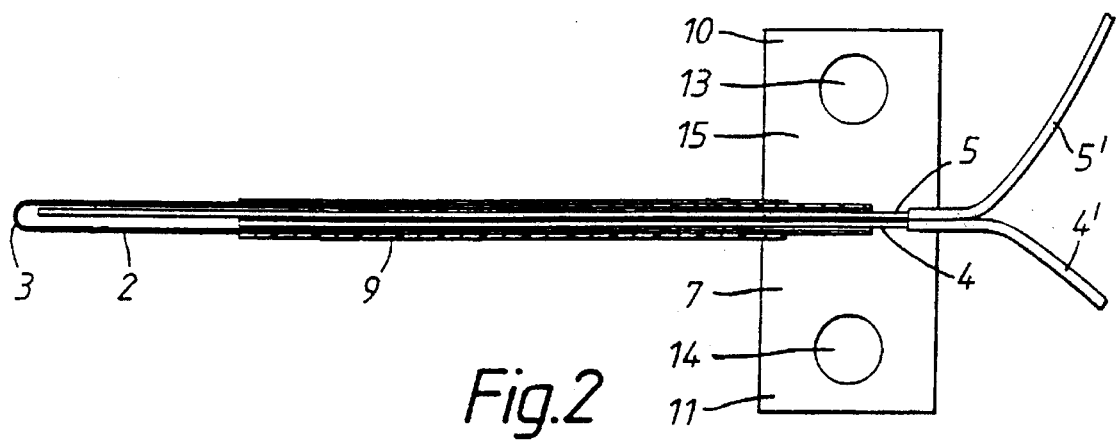
FIG. 2 shows a sectional view of the probe.

Referring to the accompanying drawings, a microdialysis probe 1 for insertion into the human or animal body comprises a tubular dialysis membrane 2 of circular cross-section and closed at its distal end, an inlet tube 4 for supplying perfusion fluid into the body of the dialysis membrane 2, and an outlet tube 5 for the exit of perfusion fluid from the body of the dialysis membrane 2. The inlet and outlet tubes 4, 5 are provided at the proximal end 6 of the tubular dialysis membrane 2 and make sealed connection with the interior of the dialysis membrane.

An anchoring member 7 is provided at the proximal end of the probe 1 and each of the dialysis membrane 2, the inlet tube 4 and the outlet tube 5 is bonded to the anchoring member 2. The anchoring member 7 includes attachment means 8 for securing it to the outside of the body of the subject.

The dialysis membrane 2 is a cellulose membrane with a cut-off of 6,000 DA (Daltons). The distal end 3 of the dialysis membrane 2 is closed by the material of the membrane itself.

One end of a flexible connecting tube 4' is connected to the proximal end of the inlet tube 4. One end of a flexible tube 5' is connected to the outlet tube 5. The said one end of each of the connecting tube 4', 5' is bonded to the anchoring member 7.

An impermeable sheath 9 is provided on the exterior of the tubular dialysis membrane 2 and extends from the proximal end 6 of the probe 1 to a position part way along the length of the dialysis membrane 2.

The tubular membrane 2 has a diameter of 0.5 millimeters, the inlet and outlet tubes a diameter of 0.2 millimeters and the overall length of the probe is approximately 7 centimeters. The sheath extends about half the length of the membrane 2 and comprises a sleeve of an elastomeric organo-silicon polymer, such as that sold under the registered Trade Mark Silastic, mounted on the dialysis membrane 2 and bonded to the anchoring member 7. The inlet and outlet tubes 4, 5 are made of a polyimide plastics material.

The dialysis membrane 2, the inlet and outlet tubes 4, 5 and the sheath 9 are all flexible.

The outlet tube 5 extends within the dialysis membrane 2 from the proximal end 6 of the probe 1 to a point within 1 centimeter of the distal end of the dialysis membrane.

The inlet tube 4 enters the proximal end of the dialysis membrane 2 and extends within the dialysis membrane just more than half the length of the dialysis membrane.

The anchoring member 7 is a resilient flexible plate-like member of plastics material, rectangular in plan, the axis of the dialysis membrane 2 being substantially parallel to the plane of the plate-like member. The inlet and outlet tubes 4 and 5 are arranged side-be-side with their axes substantially parallel to the plane of the plate-like member.

The plate-like member constituting the anchoring member 7 has first and second wings 10, 11 extending on opposite sides of the longitudinal axis of the tubular dialysis membrane 2. Each wing 10, 11 includes a respective circular aperture 13, 14 to permit suturing the probe to the subject.

The plate-like member is formed of two parts 15, 16, one part overlying the other, and the dialysis membrane 2, the inlet and outlet tubes 4, 5 and the sheath 9 are located between the two parts 15, 16.

The part 15 of the plate-like member is substantially flat and the other part 16 is substantially flat except for a central section 17 accommodating the dialysis membrane 2, the inlet and outlet tubes 4, 5 and the sheath 9.

The probe is deployed by first inserting a canula with a rupturable wall into the desired site in the subject, the probe is then inserted into the site through the canula, and then the wall of the canula is ruptured to permit removal of the canula leaving the probe in place.

Figure 3:
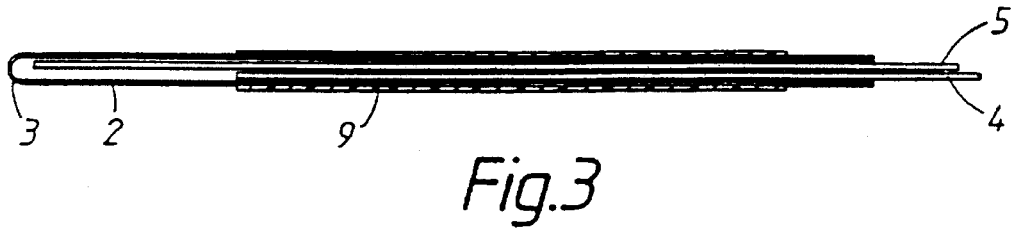
FIG. 3 shows a sectional view of a dialysis membrane, a sheath and inlet and outlet tubes of the probe.
Figure 4:
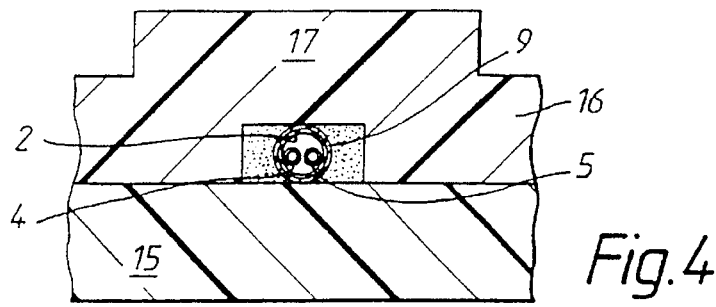
FIGS. 4 to 8 are diagrammatic partial sections to a larger scale taken along the respective sections lines IV—IV, V—V, VI—VI, VII—VII and VIII—VIII marked in FIG. 1.
Figure 5:
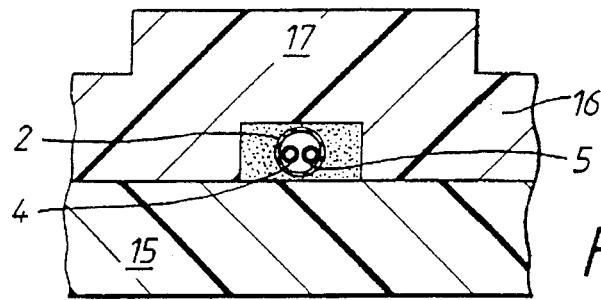

To manufacture the probe 1, the inlet and outlet tubes are inserted into the membrane 2 and then positioned on the part 15 of the anchoring member 7. The sheath 9 is then fitted over the membrane 2. The assembly positioned on the part 25 is then as shown in FIG. 3. The connecting tubes 4', 5', which are made, for example, of elastomeric organo-silicon polymer, are attached to the inlet and outlet tubes 4, 5. The whole assembly is then bonded to the part 15 using suitable adhesive. A part of each of the components 2, 4, 5, 9, 4' and 5' is joined directly to the part 15 by the adhesive and does not rely on bonding by way of one of the other components.

The part 16 is bonded into place on top of the part 15 and the other components using suitable adhesive.

Figure 6:
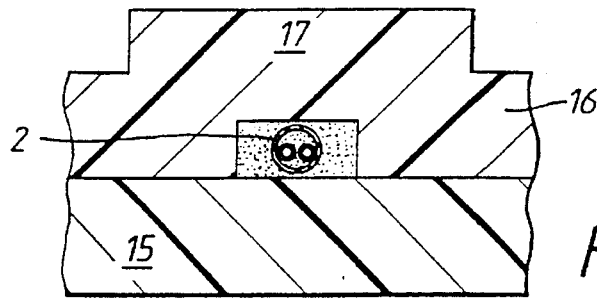
Figure 7:
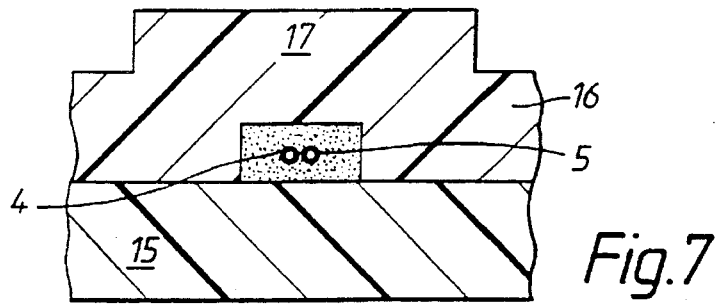
Figure 8:
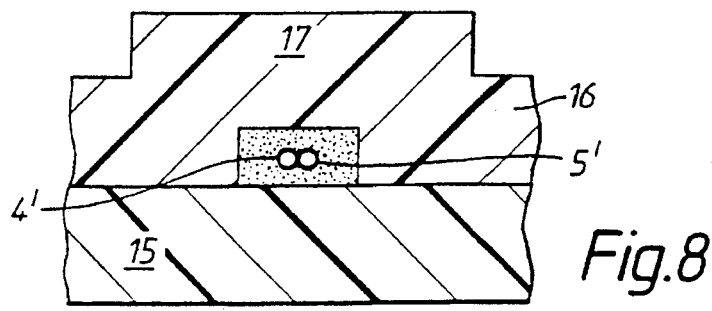

In FIGS. 4 to 8, the adhesive is represented by a series of dots and the bond surrounding each and every component can clearly be seen. Moreover, as shown in FIG. 6, the adhesive seals the tubes 4 and 5 into the mouth of the membrane 2. In FIGS. 4 to 8, the ratio of the thickness of the parts 15 and 16 to the minute diameter of the membrane 2 is shown somewhat more realistically than in the remaining figures where the membrane is shown abnormally wide in relation to the anchoring member for clarity of illustration.

A second probe embodying the invention is illustrated in FIGS. 9 and 10 and parts of the second probe corresponding to the probe of FIGS. 1 to 8 have been given identical reference numerals and will not be further described.

The probe of FIGS. 9 and 10 differs from the probe of FIGS. 1 to 8 in that it is intended for use with a cannula of the type sold under the registered Trade Marks VENFLON and ABBOCATH. Cannulas of that type include means for securing the cannula to the body of the subject and are left in situ until they are no longer required.

In the probe of FIGS. 9 and 10, the anchoring member 7 of the probe of FIGS. 1 to 8 is replaced by an anchoring member 20 secured indirectly to the body of the subject by being secured to the end of the cannula which is itself secured to the body of the subject by its own securing means. The external impermeable sheath 9 of the first embodiment is here replaced by an internal sheath 9' although, if desired, an external sheath could again be used. The anchoring member 20 is again provided at the proximal end of the probe but the dialysis membrane 2, the inlet tube 4, the outlet tube 5 and the sheath 9' project a short distance beyond it at the proximal end. The inlet and outlet tubes 4 and 5, the connecting tubes 4' and 5', and the sheath 9' are all bonded to each other close to the tip of the proximal end of the probe using a suitable adhesive, and the anchoring member 20 is bonded by a suitable adhesive to the outside of the sheath 9' and the membrane 2. Preferably, the adhesive at the tip of the proximal end of the probe is in the form of a unitary bead 25 of adhesive (shown only in FIG. 10) securing all of the inlet and outlet tubes 4 and 5, the connecting tubes 4' and 5', and the sheath 9' together. Thus, the sheath 9' is bonded directly to the anchoring member 20 and each of inlet and outlet tubes 4 and 5, and the membrane 2 are bonded indirectly to the anchoring member.

The anchoring member 20 is made of a resilient plastics material and comprises a central plug portion 21 to enter and plug the interior of the cannula, an annular head portion 22 extending transversely to the axis of the probe, and an annular wall 23 projecting from the head portion towards the distal end of the probe. The interior of the annular wall 23 is provided with a screw thread 24 for securing the anchoring member on the end of the cannula (the cannula being arranged to receive a screw cap). The exterior of the annular wall 23 is ribbed to enable it to be gripped more easily.

In one example of the second probe, the dialysis membrane had a cut-off of 10,000 Daltons and a diameter of 0.6 millimeters, the inlet and outlet tubes had a diameter of 0.1 millimeters, the impermeable sheath had a diameter of 0.5 millimeters, the overall length of the probe was approximately 15 centimeters, and the sheath extended to about 5 centimeters form the distal end of the probe.

The second probe is deployed by first inserting an intravenous cannula, such as that sold under the registered Trade Mark VENFLON, into the desired site in the subject. After withdrawal of the needle of the cannula, the probe is inserted into the lumen of the cannula until the cap-like anchoring member can be screwed (or pressed if no thread is provided) into a receiving portion of the cannula. The cannula is retained in position whilst the probe is in use.

Various modifications and alternative constructions are possible within the scope of the invention as defined by the appended claims.

In particular, the inlet and outlet tubes may be of silica or like material instead of being polyimide tubes described.

The impermeable sheath may be made of polyethylene or like material.

Instead of a sheath the corresponding region of the dialysis membrane may be treated with an impermeable coating.

Instead of having a dialysis membrane closed at its tip by its own material, a plug of adhesive material may be used to close the end of the membrane.

The probe may be short or long, minute or of moderate diameter according to the particular application for which it is intended.

Instead of making the anchoring plate in two parts and using an adhesive, the anchoring plate may be made in a single part and bonded to the components by moulding plastics material about the other components.

Where the dialysis membrane is of very fine diameter, it is possible to seal the inlet tube to the mouth of the dialysis membrane without the inlet tube entering the dialysis membrane.

Although the probe is intended to be used with the attachment means secured to the outside of the body of the subject, it may be preferred, in research on an animal subject, not to secure the attachment means to the outside of the body but instead to place the whole of the probe within the body of the subject.

It is not essential to use the tube 4 as the inlet tube and the tube 5 as the outlet tube since the probe could be operated with the tube 4 used as the outlet tube and the tube 5 used as the inlet tube.

We claim:

1. A dialysis probe for insertion into a human or animal body, the probe comprising:

a tubular dialysis membrane closed at a distal end;

an inlet tube for supplying perfusion fluid into a body of the dialysis membrane;

an outlet tube for the exit of perfusion fluid from the body of the dialysis membrane; the inlet and outlet tubes being provided at a proximal end, of the tubular dialysis membrane and making a sealed connection with an interior of the dialysis membrane;

an anchoring member is provided at the proximal end of the dialysis membrane;

each of the dialysis membrane, the inlet tube and the outlet tube is bonded to the anchoring member; and the anchoring member includes attachment means for securing it to an outside of the human or animal body.

2. A probe as claimed in claim 1, wherein the attachment means is arranged to be secured indirectly to the body of the subject and comprises a stopper surrounding the dialysis membrane for plugging a lumen of a cannula secured to the outside of the body of the subject.

3. A probe as claimed in claim 2, wherein the stopper is a cap comprising a central plug portion to enter the interior of the cannula, an annular head portion extending transversely to the axis of the probe, and an annular wall projecting from the annular head portion towards the distal end of the probe to engage the exterior of the cannula.

4. A probe as claimed in claim 3, wherein the interior of the annular wall is provided with a screw thread.

5. A probe as claimed in claim 2, wherein the dialysis membrane projects beyond the attachment means at the proximal end of the probe.

6. A probe as claimed in claim 1, wherein the attachment means is arranged to be secured directly to the body of the subject and each of the dialysis membrane, the inlet tube and the outlet tube is bonded directly to the anchoring member.

7. A probe as claimed in claim 6, wherein one end of a respective flexible connecting tube is connected to the proximal end of each of the inlet and outlet tubes, and the one said of each connecting tube is bonded to the anchoring member.

8. A probe as claimed in claim 1, wherein an impermeable sheath is provided on the interior of the exterior of the tubular dialysis membrane and extends from the proximal end of the probe to a position part way along the length of the dialysis membrane, in particular, the sheath extending to within 5, or within 2, or within 1 centimeters of the distal end of the dialysis membrane.

9. A probe as claimed in claim 8, wherein the sheath comprises an impermeable coating on the outside of the dialysis membrane, or a sleeve mounted on the dialysis membrane and bonded to the anchoring member.

10. A probe as claimed in claim 8, wherein the dialysis membrane and the sheath are both flexible.

11. A probe as claimed in claim 1, wherein the outlet tube extends within the dialysis membrane from the proximal end of the probe to a point close to the distal end of the dialysis membrane, in particular, within 5, or within 2, or within 1 centimeters of the distal end of the dialysis membrane.

12. A probe as claimed in claim 8, wherein the sheath extends to point close to but before the distal end of the outlet tube.

13. A probe as claimed in claim 1, wherein the inlet tube enters the proximal end of the dialysis membrane, in particular, extending within the dialysis membrane by more than half of the dialysis membrane.

14. A probe as claimed in claim 6, wherein the anchoring member comprises a resilient flexible plate-like member defining first and second wings extending on opposite sides of the longitudinal axis of the tubular dialysis membrane, the flexibility of the plate-like member permitting the wings to be bent together for gripping between the finger and thumb for deployment of the probe.

15. A probe as claimed in claim 14, wherein each wing includes a respective aperture to permit suturing the probe to the subject.

16. A probe as claim in claim 15, wherein the plate-like member is moulded about the dialysis membrane, the inlet and outlet tubes and, where provided, the sheath.

17. A probe as claimed in claim 15, wherein the plate-like member is formed of two parts, one part overlying the other, and the dialysis membrane, the inlet and outlet tubes and, where provided, the sheath are located between the two parts.

18. A probe as claimed in claim 1, wherein the diameter of the dialysis membrane is in the range 1 to 10, or 1 to 5, or 0.2 to 1.0, or 0.2 to 0.5, or 0.1 to 0.2, or 0.5 to 0.1 millimeters inclusive.

19. A probe as claimed in claim 1, wherein the distal end of the dialysis membrane is closed by the material of the membrane itself.

* * * * *